United States Patent [19]

Ritter

[11] Patent Number: 4,950,902

[45] Date of Patent: * Aug. 21, 1990

[54] TOOTHBRUSH STERILIZER WITH AUTOMATIC CONTROL AND METHOD

[76] Inventor: Charles H. Ritter, P.O. Box 12126, Tallahassee, Fla. 32317

[ * ] Notice: The portion of the term of this patent subsequent to Feb. 7, 2006 has been disclaimed.

[21] Appl. No.: 401,856

[22] Filed: Sep. 1, 1989

Related U.S. Application Data

[63] Continuation-in-part of Ser. No. 306,566, Feb. 6, 1989, Pat. No. 4,888,487, and a continuation of Ser. No. 21,252, Mar. 3, 1987, Pat. No. 4,803,364.

[51] Int. Cl.$^5$ .............................................. A61L 3/00
[52] U.S. Cl. ................................... 250/455.1; 422/24
[58] Field of Search ........................ 250/455.1; 422/24

[56] References Cited

U.S. PATENT DOCUMENTS

| | | | |
|---|---|---|---|
| D. 223,874 | 6/1972 | Ellis | D83/1 |
| 2,180,213 | 12/1939 | Peake | 312/207 |
| 2,245,762 | 6/1941 | Stefani et al. | 250/455.1 |
| 2,246,135 | 6/1941 | James | 250/455.1 |
| 2,350,091 | 5/1944 | Bergman | 250/455.1 |
| 2,554,152 | 5/1951 | Rosenthal | 250/455.1 |
| 2,579,242 | 12/1951 | Pask | 250/455.1 |
| 2,587,131 | 2/1952 | Ficken | 250/455.1 |
| 2,592,131 | 4/1952 | Farrar | 250/455.1 |
| 3,748,094 | 7/1973 | Scheidell | 21/83 |
| 3,776,694 | 12/1973 | Leitth | 21/102 R |
| 3,820,251 | 7/1974 | Abernathy | 34/60 |
| 3,906,236 | 8/1975 | Callahan | 250/455.1 |
| 3,954,407 | 5/1976 | Andary et al. | 21/83 |
| 4,088,455 | 5/1978 | Ellis | 21/83 |
| 4,412,134 | 10/1983 | Herold et al. | 250/504 R |
| 4,625,119 | 11/1986 | Murdock, III | 250/455.1 |
| 4,740,706 | 4/1988 | Murdock, III | 250/455.1 |
| 4,803,364 | 2/1989 | Ritter | 250/455.1 |
| 4,806,770 | 2/1989 | Hylton | 250/455.1 |

*Primary Examiner*—Jack I. Berman
*Attorney, Agent, or Firm*—Shlesinger & Myers

[57] ABSTRACT

A toothbrush conditioning device comprises a body member having an upper end; a cover member having a first orientation mounted to the upper end for forming with the cover member a conditioning chamber and a second orientation remote from the upper end for providing access to the body member; lamp means disposed proximate the toothbrush for conditioning the toothbrush when the cover member is in the first orientation; fan means for ventilating the chamber; control means operably associated with the lamp means and the fan means for causing automatic intermittent operation of the lamp means and for causing automatic operation of the fan means for a preselected time when the cover member is in the first orientation; and switch means operably associated with the cover member, the body member and the control means for permitting operation of the control means, the lamp means and the fan means when the cover member is in the first orientation and for preventing operation thereof when the cover member is in the second orientation. The body member also includes an apertured plate for selectively positioning within the chamber a toothbrush to be conditioned.

20 Claims, 6 Drawing Sheets

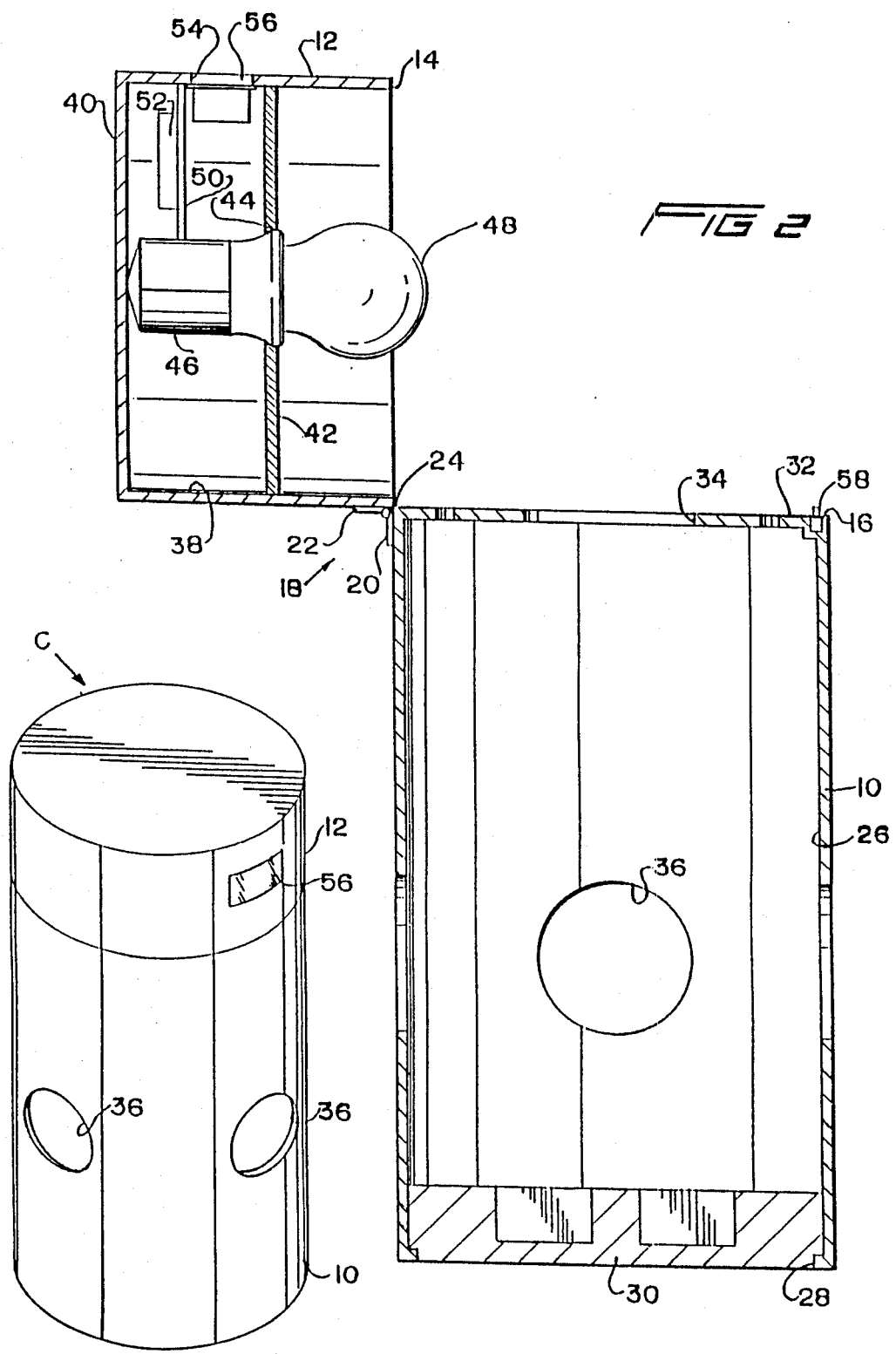

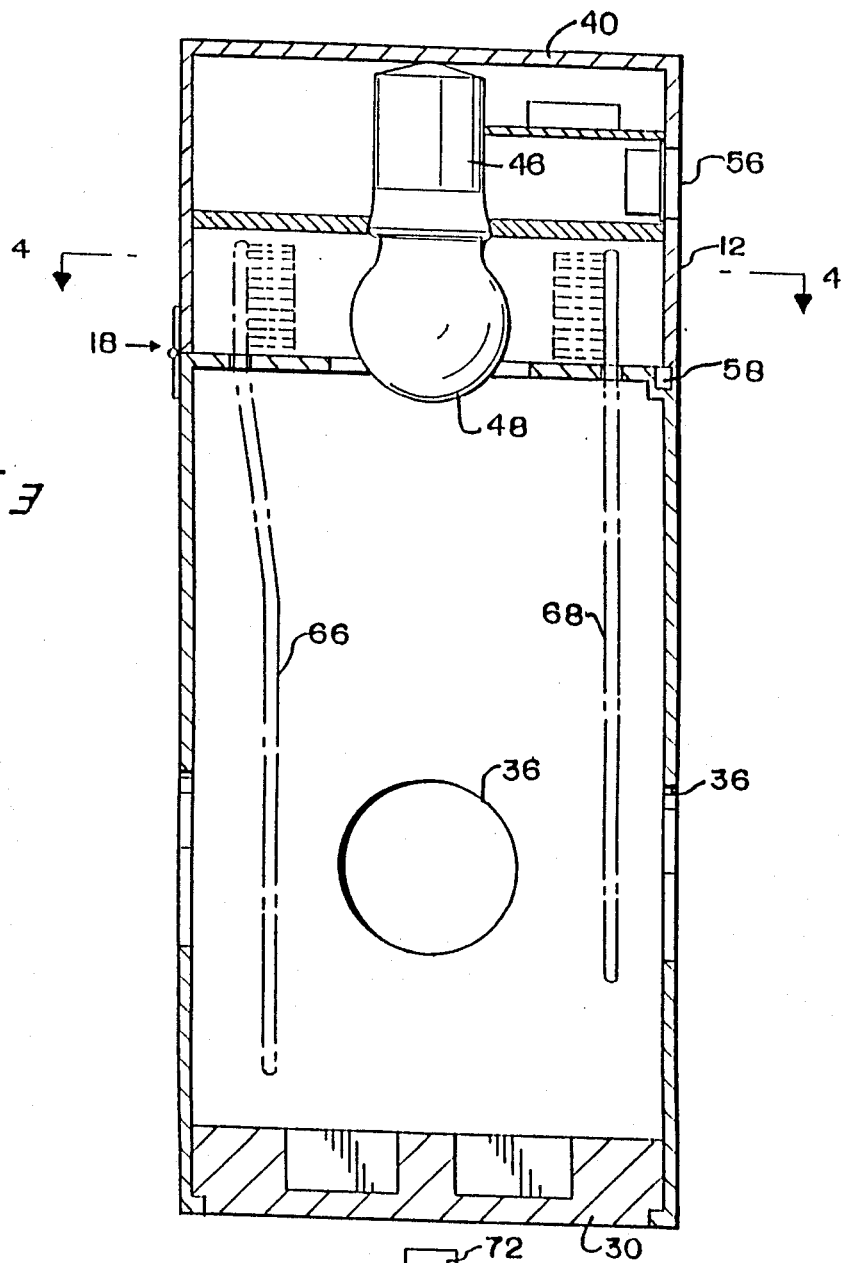
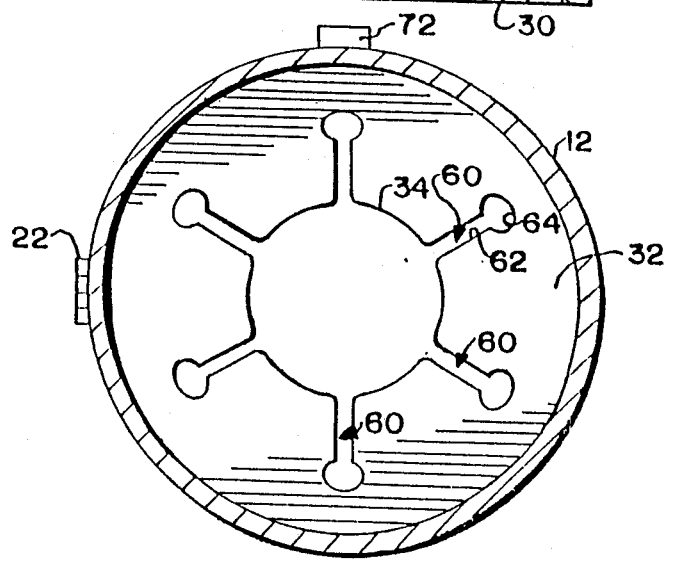
FIG 3
FIG 4

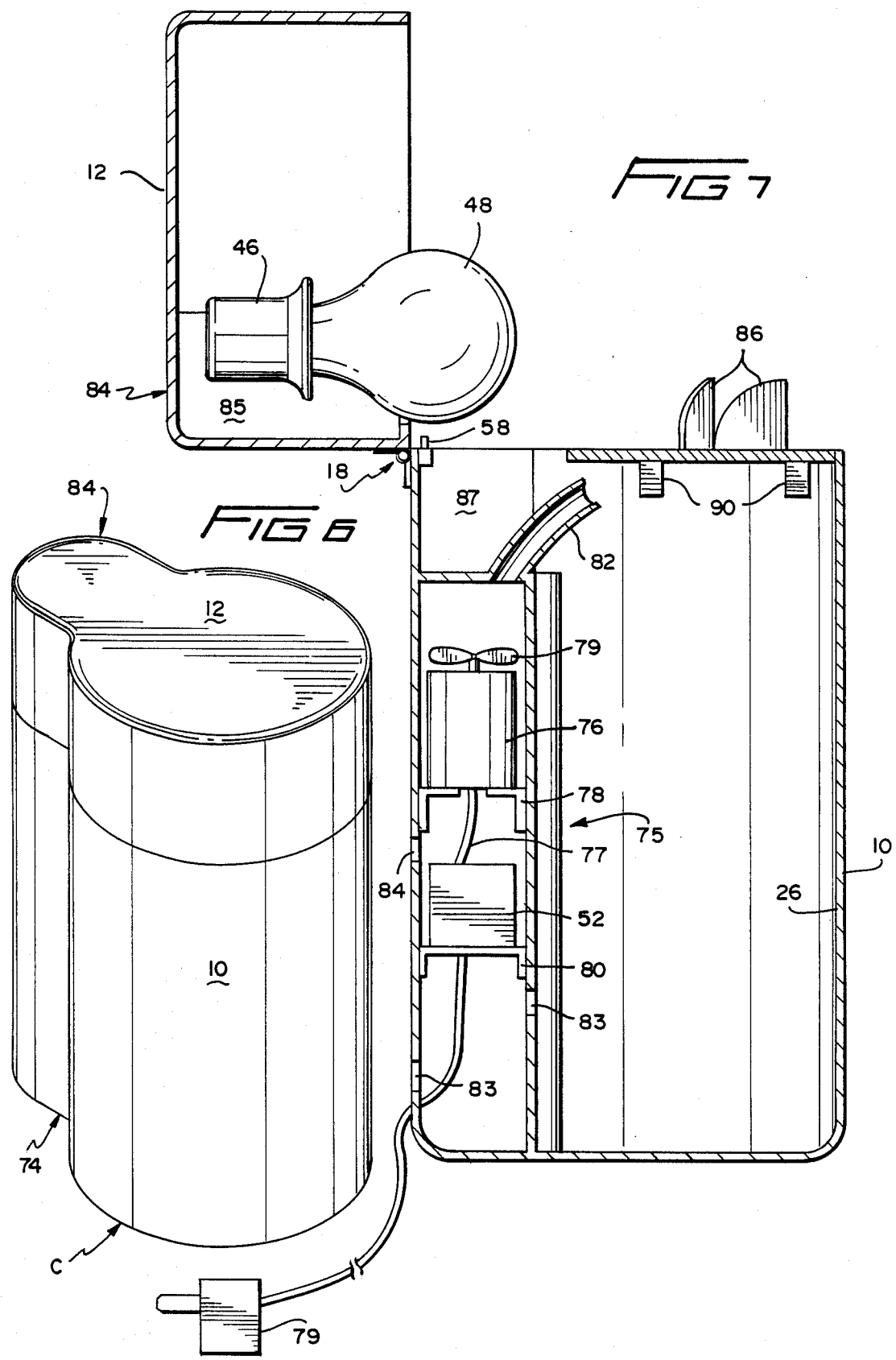

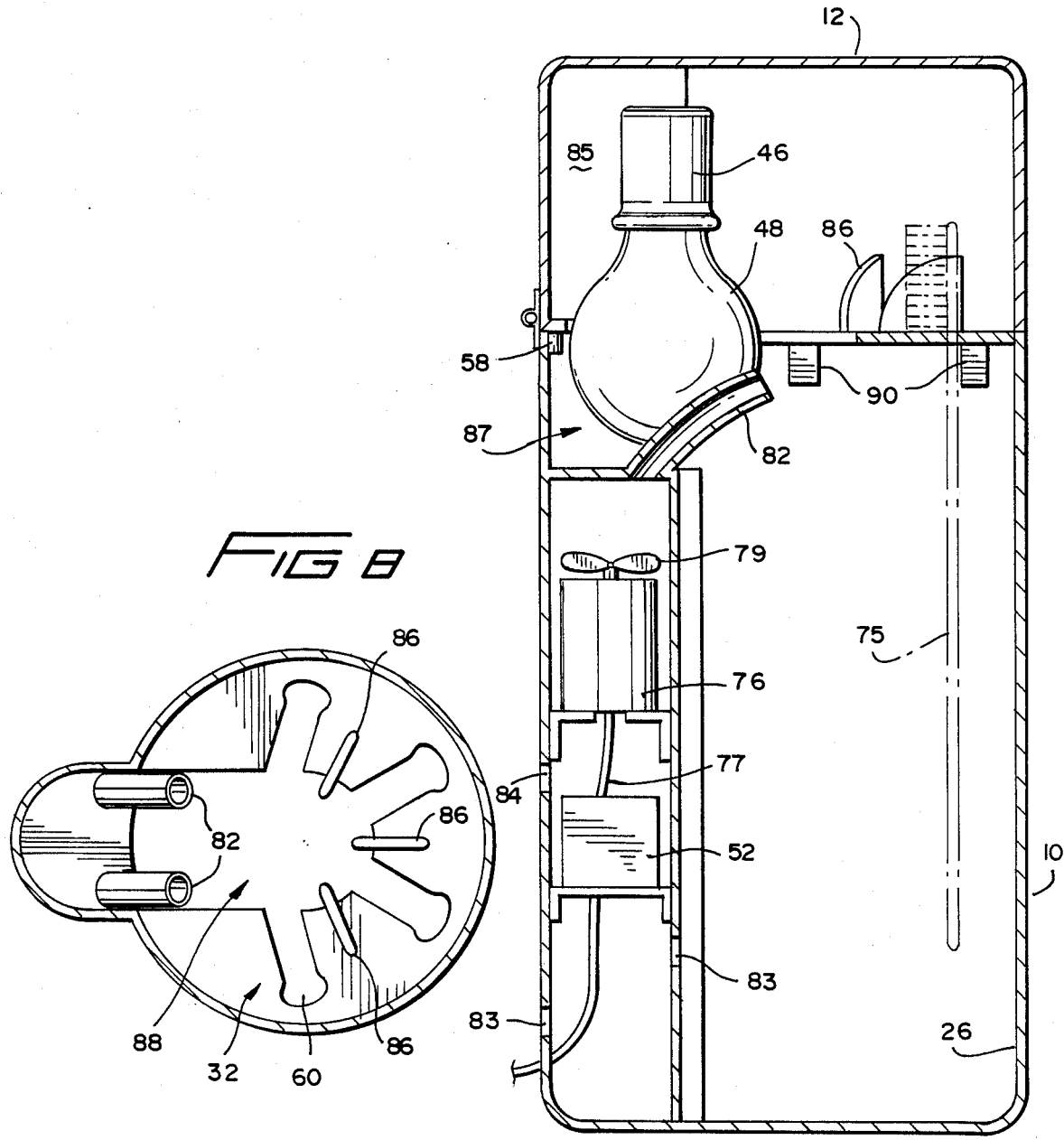

TOOTHBRUSH STERILIZER WITH AUTOMATIC CONTROL AND METHOD

RELATED INFORMATION

This application is a continuation-in-part of application Ser. No. 07/306,566, filed on Feb. 6, 1989, now U.S. Pat. No. 4,888,489 which is a continuation of Application Ser. No. 07/21,252, filed on Mar. 3, 1987, now U.S. Pat. No. 4,803,364.

BACKGROUND OF THE INVENTION

An intern virus may remain alive on a countertop for up to several hours, thereby permitting those who come into contact with the countertop to run the risk of infection. Also, many people have frequent bleeding from the gums, which can otherwise transfer blood and contaminants therein to the toothbrush which they use. It is common for the user of a toothbrush, particularly when at the work place, to leave the brush in a publicly accessible place, such as on a restroom countertop or the like. In that location, the toothbrush is then capable of being contaminated by any local intern virus, as well as free to be contaminated by insects and the like, or may itself contaminate the countertop.

The prior art discloses a number of devices for sterilizing or otherwise conditioning a toothbrush by means of radiant energy. The most common radiant energy source is an ultraviolet lamp. Ultraviolet radiation is used because of its sterilizing effect. Ultraviolet radiation is used because of its sterilizing effect. Ultraviolet radiation produces a violent vibration in the cell walls of microbes, causing them to rupture and kill the organism.

Two basic types of ultraviolet toothbrush conditioners are known. The first operates continuously, thereby acting more as a still than a sterilizer. The other type operates in an on-off way, thereby running the risk that the brush is not properly conditioned before a subsequent use. Neither of these types appreciates the problem of vapor condensation at the top of the device, which condensation provides a source for continued contamination.

In view of the above, it can be seen that there is a need for a toothbrush conditioner which effectively destroys contaminating microbes and the like by bombardment with radiant energy of a selected wavelength. Preferably, the conditioner optimally balances the relevant thermodynamic relationships to assure that the vapor is driven away from the brush so as to exit the device, thereby drying the bristles and avoiding subsequent contamination through condensation. The disclosed invention is just such a conditioner and satisfactorily avoids the problems of the prior art.

OBJECTS AND SUMMARY OF THE INVENTION

The primary object of the disclosed invention is to provide an ultraviolet wavelength toothbrush conditioner which has optimum thermodynamic design in order to drive the moisture away from the bristles and out of the conditioning chamber.

The toothbrush conditioning device of the invention includes a body member having an upper end. A cover member is removably mounted to the upper end and forms with the body member a conditioning chamber. A plate is mounted in the body member for selectively positioning within the chamber a toothbrush to be conditioned. An ultraviolet radiation source is carried by the cover member and is movable therewith so that the source is selectively positioned within the chamber proximate a brush or brushes to be conditioned when the cover member is mounted to the upper end. A plurality of openings are in the body member for permitting water vapor to vent from the chamber. A programmable timer and switch mechanism are provided for intermittently operating the radiant source for a selected period when the cover member is mounted to the upper end.

These and other objects and advantages of the invention will be readily apparent in view of the following description and drawings of the above described invention.

DESCRIPTION OF THE DRAWINGS

The above and other object and advantages and novel features of the present invention will become apparent from the following detailed description of the preferred embodiment of the invention illustrated in the accompanying drawings, wherein:

FIG. 1 is a perspective view illustrating my toothbrush conditioner;

FIG. 2 is a longitudinal cross-sectional view thereof with the cover member shown in the pivoted position;

FIG. 3 is a cross-sectional view with the cover member shown in the closed position, and with toothbrushes shown in phantom lines;

FIG. 4 is a cross-sectional view taken along the section 4—4 of FIG. 3, and viewed in the direction of the arrows, and with the toothbrushes omitted for the sake of clarity; and, FIG. 5 is an elementary schematic view of the control circuitry of the invention;

FIG. 6 is a perspective view illustrating another embodiment of my toothbrush conditioner;

FIG. 7 is a longitudinal cross-sectional view my toothbrush conditioner depicted in FIG. 6 with the cover shown in the pivoted position;

FIG. 8 is a cross-sectional view with the cover member shown in the closed position, and with the toothbrush shown in phantom lines;

FIG. 9 is a cross-sectional view taken along the section 8—8 of FIG. 8, and viewed along the direction of the arrows, and with the toothbrushes and the lamp omitted for the sake of clarity.

DESCRIPTION OF THE INVENTION

Figure 5:
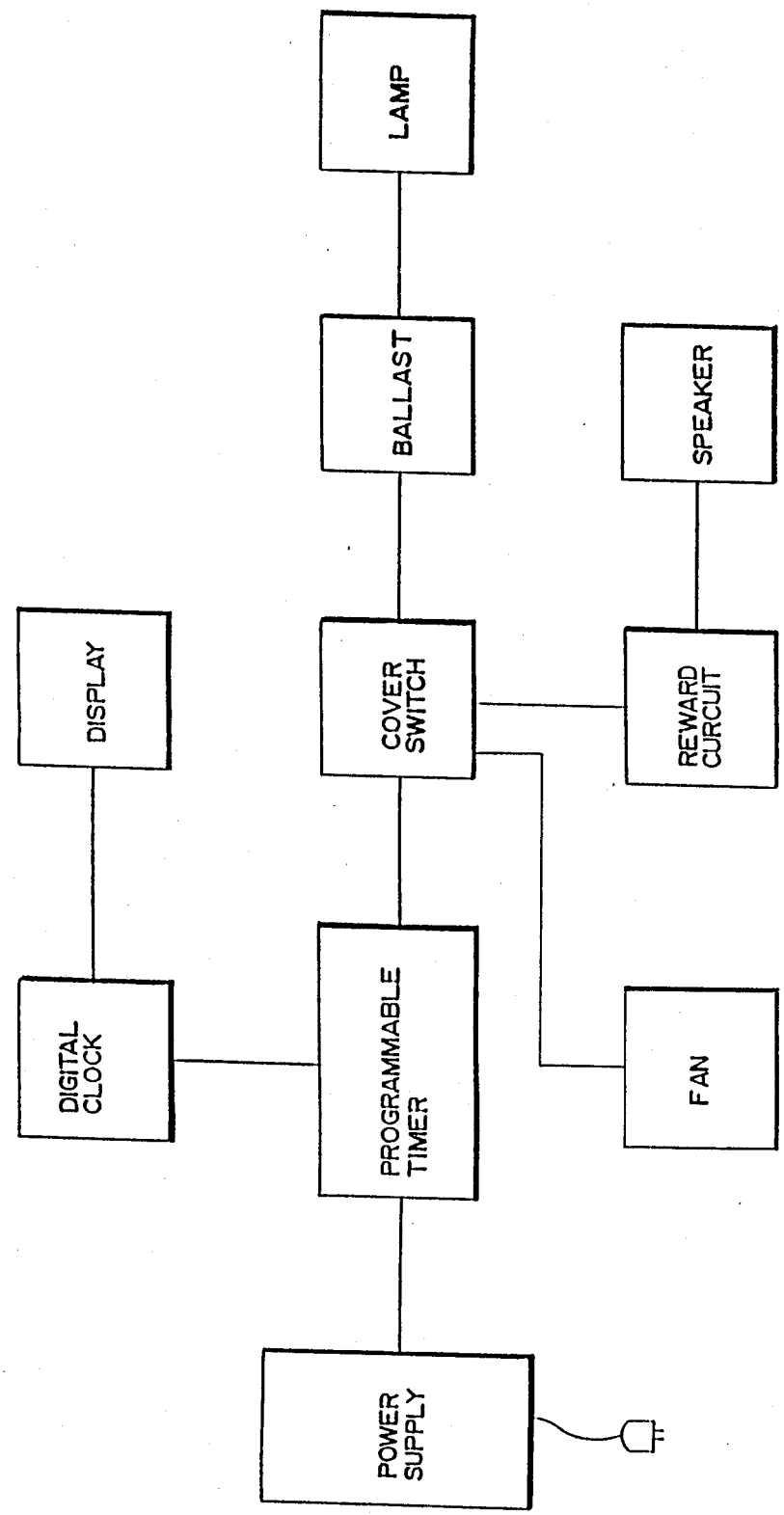

Conditioner C, as best shown in FIGS. 1–3, is a cylindrical device, although other configurations may be appropriate in certain instances. The conditioner C includes a body member 10 and a cover member 12. Preferably, the body and cover members 10 and 12, respectively, have a uniform diameter so that the lower edge 14 of the cover member 12 seats with the upper end edge 16 of body member 10. It is to be noted in FIGS. 2 and 3 that the body member 10 has a length substantially in excess of the length of cover member 12, the body member 10 having a length substantially corresponding to the length of a toothbrush. Each of the body and cover members 10 and 12, respectively, is comprised of an opaque plastic material, although other materials and coloring may be appropriate. I prefer an opaque material for the exterior of the conditioner C in order to minimize any hazard which could occur from exposure to ultraviolet radiation.

Hinge 18 has a first leaf 20 secured to body member 10 and a second leaf 22 secured to cover member 12. Naturally, the hinge 18 includes a pivot pin 24 to permit the cover and body members 12 and 10, respectively, to pivot relative to each other, and the pivot pin 24 is aligned with the upper edge 16 of the body member 10. In this way, the cover member 12 may be pivoted from the closed position illustrated in FIG. 3, to the open position illustrated in FIG. 2.

Body member 10 has a central aperture 26 therethrough which is closed at lower end 28 by member 30. The member 30 may be used for supporting the conditioner C on a countertop, or the like. Support plate 32 extends across upper end edge 16 and has a central aperture 34 for reasons to be explained. Preferably, the support plate 32 is integral with or secured to body member 10. The plate 32 may be comprised of an opaque plastic, although a clear plastic is preferred for increased conditioning effect within the body chamber. Body member 10 also includes a plurality of vent openings 36, as will be further explained.

Cover member 12 has an aperture 38 therethrough which is closed by top member 40. In this way, pivoting of the cover member 12 into the closed position of FIG. 3 provides a conditioning chamber in cooperation with the body member 10.

A support member 42 extends parallel to top member 40 and is disposed intermediate lower edge 14 and top member 40. Support member 42 includes an aperture 44 therethrough in which socket 46 is secured. Ultra-violet lamp 48 is removably secured in the socket 46, in a manner well known in the art. The socket 46 is centrally positioned relative to cover member 12 so that the lamp 48 is likewise centrally positioned.

Secondary support 50 extends from socket 46 to the wall of cover member 12 above support member 42. Control device 52, which may include a modern electronic control mechanism, is mounted to secondary support 50. The conventional wiring and connections for the control device 52 are omitted for the sake of clarity. Control device 52 is positioned within cover member 12 15 in order to minimize the wire lengths and increase compactness.

Opening 54 is disposed in the side wall of member 12, and is disposed between secondary support 50 and support member 42. Display 56 is positioned in opening 54 and is in operative connection with control device 52 by means not shown. Display 56 preferably includes a digital clock or the like, in order to facilitate programming of the control device 52. FIGS. 2 and 3 disclose switch assembly 58 which extends axially upwardly from the sidewall of the body member 10. The switch assembly 58 is aligned with the lower edge 14 and is engageable therewith when the cover member 12 is in the closed position of FIG. 3. The switch assembly 58 is in operative connection, by means not shown, with the control device 52. Engagement of the lower edge 14 with the switch assembly 58 indicates to the control device 52 that the cover member 12 is in the closed position, thereby permitting the lamp 48 to be operated at the appropriate time, as will be further explained. Naturally, switch assembly 58 could just as easily extend from edge 14.

FIG. 4 discloses slots 60 extending radially from central aperture 34 in support plate 32. Each of the slots 60 extends through the support plate 32 and includes a relatively straight portion 62 and an oval enlarged portion 64. The slots 60 communicate with the central aperture 34 in order to permit a toothbrush, such as the toothbrushes 66 and 68 of FIG. 3, to be supported by support plate 32.

Each of toothbrushes 66 and 68 is aligned for insertion with the respective portion 62 and is moved radially therealong until the toothbrush may be rotated upon being positioned within the enlarged portion 64. A typical toothbrush, such as 66 or 68, has a bristle-carrying head. The neck has a reduced width. The enlarged area 64 has a diameter less than the width of the head, so that the head will rest upon the adjacent portions of the plate 32 and thereby be maintained at the proper positioning for further conditioning. This prevents the bristles from resting upon the plate and becoming bent. Removal of the toothbrush from the enlarge portion 64 merely requires that the brush be rotated and then slid through the respective straight portion 62 until the opening 34 is reached, thereby permitting removal.

FIG. 5 discloses an elementary schematic diagram illustrating the control circuit of the invention as provided by the control device 52 and the related assemblies. A power supply has an electric cord with a plug for permitting connection with a source of electric power. Although a plug 70 is illustrated in FIG. 5, those skilled in the art will understand that a battery source is also possible. The power supply includes the appropriate voltage and current regulating devices as may be required.

The power supply is connected with a programmable timer which causes the lamp 48 to be operated for a preselected duration upon the passage of a selected interval. As noted, I have found that continuous operation of the conditioner C is not required, it merely being necessary for the lamp 48 to operate for the appropriate period of time required to destroy the contaminants. Intermittent operation is desirable in order to avoid the humidor-like effects that can occur from continuous operation. Intermittent operation of the lamp 48 also assures that the bristles of the toothbrush are not prematurely degraded by the conditioning effects of the ultraviolet radiation.

A cover switch, such as the switch assembly 58, is in operative connection with the programmable timer and permits the lamp 48 to be operated only when the cover member 12 is in the closed position. The cover switch therefore prevents the user from being exposed to the ultraviolet radiation should the cover member 12 be lifted during a burn cycle. The ballast for the lamp 48 is likewise in connection with the cover switch and is of a type well-known in the art.

The programmable timer is also connected with a digital clock in order to display the time to the user through the display 56. The display 56 therefore avoids the need for a bathroom clock, and also permits the user to set the programmable timer when the conditioner C is initially installed.

FIG. 5 also discloses a reward circuit and an audio speaker which may be appropriate in a conditioner C directed for use by children. The reward circuit generates some sort of audio encouragement to the child user upon his use of the conditioner C, as well as of the appropriate toothbrush. The prior art discloses certain forms of audio synthesis techniques, such as by computer chips and the like, which can be easily adapted for use with the circuit of FIG. 5. It is well-known that it is difficult to get children to use their toothbrush on a regular basis, and the reward circuit will therefore increase a child's use, as well as make sure that he uses a properly conditioned toothbrush.

I have designed the conditioner C in order to obtain drying of the toothbrush, while also achieving reduction, essentially elimination, of interchamber condensation. The thermodynamic design of the conditioner C is such that the hottest point in the chamber is at the highest point. Naturally, the lamp 48 provides this hot point and, because of its location adjacent the support member 42, is appropriately arranged for maximizing the temperature at the upper end of the chamber. Because the hottest point is at the highest point in the chamber, a downward flow of the moisture laden vapor from the toothbrush is caused to occur. This downward moisture flow communicates through the straight portions 62 and the central aperture 34, until the moisture exits through the vent openings 36. The vent openings 36 are relatively large in order to create a draft for vapor removal, thereby preventing the moisture laden vapor from condensing on the bottom of support member 42.

I have found that there is minimal risk of brush contamination from ambient room air, particularly when the cover member 12 is in the closed position. Furthermore, a finite period is required for colonization of the bristles after contamination and intermittent operation of the lamp 48 is set to occur frequently enough to prevent this colonization. Therefore, any ambient contamination is destroyed before subsequent use. Furthermore, although I disclose that the lower end 28 of the body member 10 is closed by member 30, this is not necessary and an open end further reduces the risk of condensation contamination. Also, an open end more easily permits the interior of the conditioner C to be cleaned.

I prefer that the lamp 48 be of the globe-like configuration in order to provide substantially uniform radiation of the surrounding toothbrushes. Furthermore, the lamp 48 is carried by the cover member 12 in order to pivot the lamp 48 away from the cover plate 32 when a toothbrush is being inserted or removed from the conditioner C. In this way, the risk of a wet brush contacting a hot lamp 48 is minimized, thereby avoiding premature lamp failure or even breakage. It is to be noted in FIG. 3 that the lamp 48 extends through the central aperture 34 in order to make sure that the air within the body member 10 is heated and driven through the vent openings 36, and that the brush handle is conditioned by the radiation. Furthermore, should the plate 32 be transparent, then the radiation will pass therethrough into the chamber of body 10, thereby destroying contaminants on the brush handle.

FIG. 4, discloses a bracket 72 extending from the side wall of the body member 10. The bracket 72 may be used to provide a wall mounted conditioner C. Should the conditioner C be wall mounted, then it may be desirable to provide an external jacket surrounding the body member 10 in order to prevent the user from peering into the conditioner C through the vent openings 36, and thereby being exposed to the ultraviolet radiation. Naturally, the jacket has a diameter exceeding that of the body member 10 and thereby acts as a flue so that the warmer air exiting from the conditioner C moves upwardly along the jacket interior surface.

ALTERNATE EMBODIMENT

In another embodiment of my present invention, the body member 10 includes an integral longitudinal portion 74, as best shown in FIGS. 6, 7, 8, 9 and 10. The extension portion 74 includes a chase 75. An electric fan 76 with impeller 79 and the control device 52 are disposed within the chase 75. Suitable brackets 78 and 80 support the fan 76 and the control device 52 therein, respectively. Except for air outlets 82 and air exhaust outlet 83, the chase 75 is completely sealed from the central aperture 26, thereby keeping any excessive moisture from the toothbrush 75 being conditioned from adversely affecting the fan 76 and the control device 52. Also, heat and radiation from the lamp 48 is kept away from the fan 76 and the control device 52. Wires 77 operably connects the fan 76 to the control device 52. Power supply 79 provides power to the control device 52 and thereby to the fan 76 and the lamp 48. The chase 75 includes an air inlet 84, disposed downstream of the fan 82 and the air outlets 82. Moisture-laden air exits through exhaust outlets 83 which are disposed in the chase 75 and below the air inlet 84. The exhaust outlets 83 are advantageously staggered from each other in order to prevent any light leakage from the lamp 48.

The longitudinal portion 74 further includes a berth 87 disposed above the chase 75 and in communication with the aperture 26 for accommodating the lamp 48 when the cover member 12 is in the closed position, as best shown in FIGS. 7, 8 and 9. When positioned within the berth 87, the lamp 48 is unobstructed in the direction of the toothbrushes, thereby permitting the lamp 48 to properly irradiate the toothbrushes for sterilization.

The cover member 12 also includes an extension portion 84 forming a compartment 85 in which the lamp socket 46 is disposed. The extension portion 84 is integral with the cover member 12, as best shown in FIGS. 6, 7 and 9.

The hinge 18 permits the cover member 12 to pivot between the closed and open positions relative to the body member 10. The body member 10 and the cover member 12 have the same exterior shape so that the body member 10 is flush with the cover member 12 in the closed position.

The switch assembly 58 is disposed adjacent the hinge 18 and is operative with the closing and opening of the cover member 12.

Figure 10:
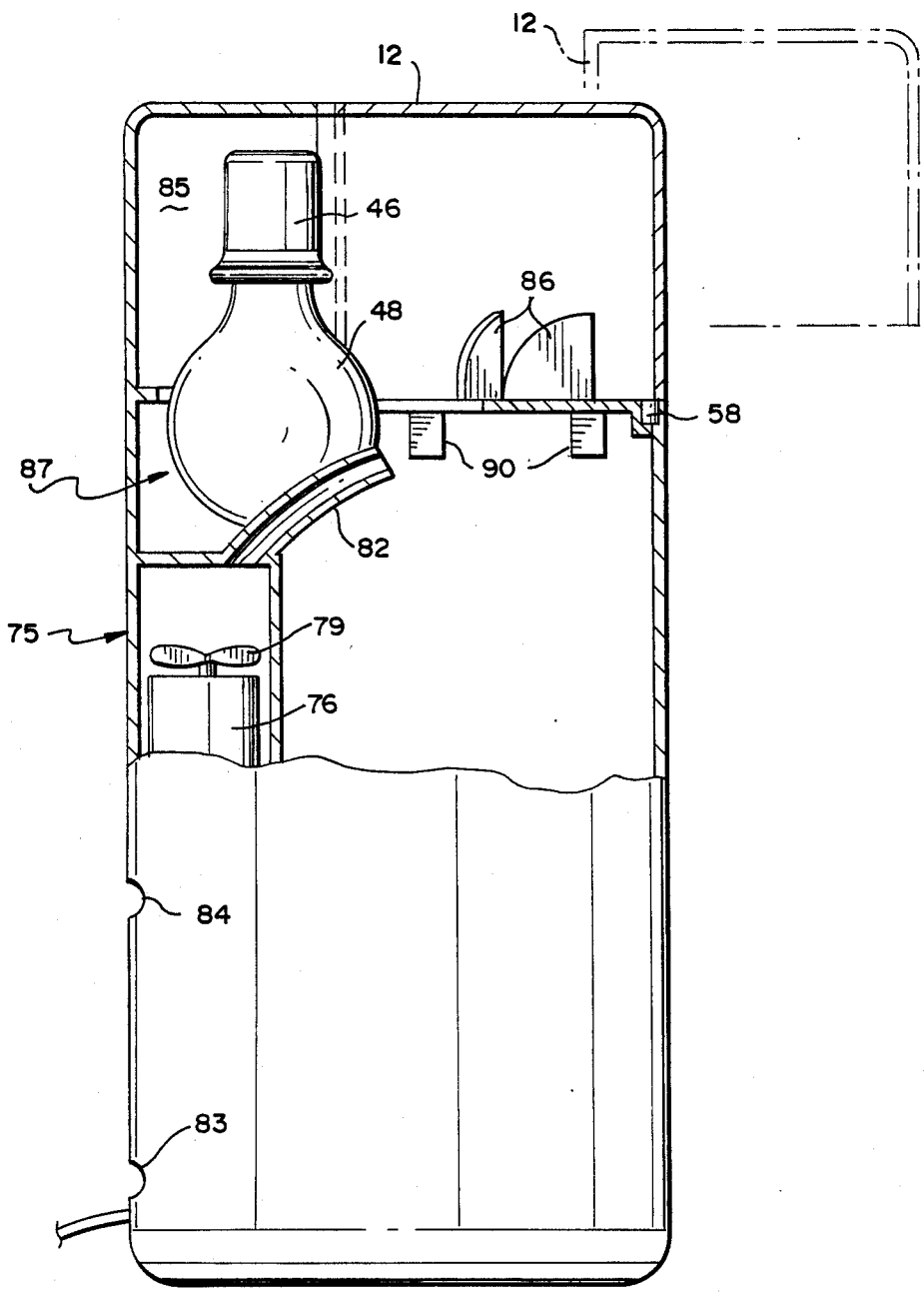
FIG. 10 is a side elevational view of another embodiment of my toothbrush conditioner, portions of which are shown broken-away in cross-section and in phantom lines, illustrating a non-pivotal cover member in the closed and open positions.

The extension portion 84 is disclosed in FIG. 10 as integral with the body member 10, and forming a part of the longitudinal portion 74. In this case, the lamp 48 is not carried by the cover member 10, but is fixed to the body member 10. Also, the cover member 12 is not hingedly secured to the body member 10, but is simply removable therefrom. Interlocking edges, such as tongue and groove arrangement (not shown) associated with the cover member 12 and the body member 10 provides means for securing the cover member 12 to the body member 10 when in the closed position. Switch assembly 58 is appropriately located for engagement with the cover member 12 when it is in the closed position.

Support plate 32 includes dividers 86 disposed substantially transverse thereto and substantially mid-way each adjacent pairs of the slots 60. The support plate 32 also includes a radial aperture 88 extending from and communicating with the berth 85 and terminating substantially at the center of the support plate 32. The aperture 88 is wide enough to accommodate the width of the lamp 48 which passes through the aperture 88 when the cover member 12 is pivoted between the closed and open positions. The support plate 32 is removable and is supported by brackets 90 which are preferably integral with the body member 10. The removable feature of the support plate 32 permits access to the central aperture 26 for periodic cleaning thereof.

The longitudinal extension 74 provides the body member 10 with a footprint which is stable and thereby prevents tipping.

OPERATION

Operation of the conditioner C is essentially automatic once the power supply is connected to a power source. Naturally, the user will set the digital clock upon initial installation, thereby automatically determining when the lamp 48 will be operated. As noted, the control device 52 automatically causes the lamp 48 to be illuminated, except in those instances when the cover member 12 is in the open position. Even then, should the cover member 12 be raised during a burn cycle, then operation of the lamp 48 will only be stopped for that period of time that the cover member 12 is raised, and will commence again as soon as the cover member 12 is lowered.

The user need merely to pivot the cover member 12 into the open position of FIG. 2 in order to insert a toothbrush into the conditioner C. As previously noted, the brush is initially lowered through the opening 34 and is aligned with one of the straight portions 62. The brush is then moved radially until the respective enlarge portion 64 is reached, at which point the brush is rotated. The brush is then supported by the adjacent portions of the cover plate 32, thereby appropriately positioning the brush for conditioning. The cover member 12 is then closed, thereby permitting the control device to operate the lamp 48 as specified by the circuitry.

Subsequent use of the conditioned toothbrush is easily accomplished by pivoting of the cover member 12 into the opened position. This pivoting moves the lamp 48 out of the chamber area. The user may then grasp the appropriate toothbrush without fear of burning his hand on the lamp 48. The brush, when grasped need merely be rotated so that the hand thereof may be caused to pass through the respective straight portion 62, and ultimately 10 removed through the central opening 34. The cover member 12 may then again be closed so that any other remaining toothbrushes may be conditioned, as dictated by the control circuit 52.

The reward circuit and speaker of FIG. 5 are appropriate for conditioners C directed towards children. In that instance, the speaker plays a particular message when the cover member 12 is lifted. Likewise, the speaker plays a particular message when the cover member 12 is again closed. The messages acknowledge and encourage the use of the conditioner C by the child, and implicitly use of the toothbrush.

Referring to FIGS. 6 through 10, the switch 58 is activated by the closing of the cover member 12. The fan 76 subsequently operates for a predetermined period of time, pulling room air through inlet 84 and discharging it through outlets 82. Air laden with moisture from the toothbrush 75 being conditioned exits through the exhaust outlets 83 which are in communication with the aperture 26. The outlets 82 are substantially directed at the toothbrush 75 being conditioned, thereby aiding in the drying process. At the same time, the lamp 48 operates in the manner as previously described for sterilizing the toothbrush 75. The time of operation of the fan 76 is adjustable by means of the control circuit 52. The fan 76 operates continuously for a period of time and then shuts off until it is restarted by the opening and closing of the cover member 12, while the lamp 48 operates independently in a manner previously described. The fan 76 operates continuously for a longer period than each ON period of the lamp 48. For example, the lamp 48 might operate for 1½ minutes for every 30 minutes while the fan 76 might operate continuously for 30 minutes. When the cover member 12 is opened, thus disengaging the switch 58, the fan 76 stops if it happens to be running. The fan 76 cannot operate while the cover member 12 is in the open position. The lamp 48 is also turned off when the cover member 12 is opened, as previously described. When the cover member 10 is replaced back to its closed position, the fan 76 is again activated for a predetermined period and the lamp 48 operates as previously described.

While this invention has been described as having a preferred design, it is understood that it is capable of further modifications, uses and/or adaptations of the invention following in general the principle of the invention and including such departures from the present disclosure as come within known or customary practice in the art to which the invention pertains, and as may be applied to the central features hereinbefore set forth and fall within the scope of the invention of the limits of the appended claims.

I claim:

1. A method for conditioning a toothbrush, comprising the steps of:
   (a) providing a conditioning chamber;
   (b) positioning the toothbrush to be conditioned inside said chamber;
   (c) providing means within said chamber and proximate the toothbrush for conditioning the toothbrush; and
   (d) automatically intermittently controlling said conditioning means.
2. A method as in claim 1, wherein:
   (a) said controlling includes controlling with a timer.
3. A method as in claim 1, and including the step of:
   (a) ventilating for a predetermined period.
4. A method as in claim 3, wherein:
   (a) said ventilating includes ventilating with a fan.
5. A method as in claim 4, wherein:
   (a) said ventilating includes controlling the fan with a timer.
6. A method as in claim 3, wherein:
   (a) said ventilating includes ventilating with a fan for a period exceeding the period that the conditioning means is operating.
7. A toothbrush conditioning device, comprising:
   (a) a body member having an upper end;
   (b) a cover member;
   (c) said cover member having a first orientation mounted to said upper end for forming with said cover member a conditioning chamber and a second orientation remote from said upper end for providing access to said body member;
   (d) said body member including means for selectively positioning within the chamber a toothbrush to be conditioned;
   (e) means disposed proximate the toothbrush for conditioning the toothbrush when said cover member is in said first orientation;

(f) fan means for ventilating said chamber;

(g) control means operably associated with said conditioning means and said fan means for causing automatic intermittent operation of said conditioning means and for causing automatic operation of said fan means for a preselected time when said cover member is in said first orientation; and (h) switch means operably associated with said cover member, said body member and said control means for permitting operation of said control means, said conditioning means and said fan means when said cover member is in said first orientation and for preventing operation thereof when said cover member is in said second orientation.

8. A toothbrush conditioning device as in claim 7, wherein:

(a) said body member includes an extension portion; and (b) said extension portion includes a chase substantially sealed from said chamber.

9. A toothbrush conditioning device as in claim 8, wherein:

(a) said cover member includes an extension portion for forming a compartment; and (b) said conditioning means is supported from said compartment.

10. A toothbrush conditioning means as in claim 9, wherein:

(a) said body member extension portion includes a berth disposed above said chase and is in communication with said chamber; and (b) said conditioning means is disposed within said berth when said cover member is in said first orientation.

11. A toothbrush conditioning means as in claim 8, wherein:

(a) said fan means and said control means are disposed within said chase.

12. A toothbrush conditioning device as in claim 11, wherein:

(a) said chase includes air inlet, air outlet and exhaust outlet;

(b) said air outlet is directed toward said chamber; and (c) said air outlet is adjacent said conditioning means, thereby causing heating of air discharging from said air outlet and aiding in the drying of the toothbrush to be conditioned.

13. A toothbrush conditioning device as in claim 7, wherein:

(a) said switch means is disposed proximate said upper end and is engageable with said cover member when said cover member is in said first orientation; and (b) said cover member has a lower end portion and said lower end portion is engageable with said switch means.

14. A toothbrush conditioning device as in claim 10, wherein:

(a) said positioning means includes an apertured surface;

(b) said surface has a plurality of apertures and one of said apertures is in communication with said berth; and (c) a portion of said conditioning means extends through said communicating aperture and downwardly beyond said surface when said cover member is in said first orientation.

15. A toothbrush conditioning device as in claim 14, wherein:

(a) said positioning means includes dividers disposed transversely from said surface; and (b) each of said dividers is disposed between adjacent pairs of said other apertures.

16. A toothbrush conditioning device, comprising:

(a) a body member having an upper end;

(b) a cover member;

(c) said cover member having a first orientation mounted to said upper end for forming with said cover member a conditioning chamber and a second orientation remote from said upper end for providing access to said body member;

(d) said body member including means for selectively positioning within the chamber a toothbrush to be conditioned;

(e) lamp means disposed proximate the toothbrush for conditioning the toothbrush;

(f) fan means for ventilating said chamber;

(g) control means operably associated with said lamp means and said fan means for causing automatic intermittent operation of said lamp means and for causing automatic operation of said fan means for a preselected time when said cover member is in said first orientation; and (h) switch means operably associated with said cover member, said body member and said control means for permitting operation of said control means, said lamp means and said fan means when said cover member is in said first orientation and for preventing operation thereof when said cover member is in said second orientation.

17. A toothbrush conditioning device as in claim 16, wherein:

(a) said body member includes an extension portion;

(b) said extension portion includes a chase substantially sealed from said chamber;

(c) said body member extension portion includes a berth disposed above said chase an is in communication with said chamber; and (d) said lamp means is disposed within said berth.

18. A toothbrush conditioning device as in claim 17, wherein:

(a) said fan means and said control means are disposed within said chase;

(b) said chase includes air inlet, air outlet and exhaust outlet;

(c) said air outlet is directed toward said chamber; and (d) said air outlet is adjacent said lamp means, thereby causing heating of air discharging from said air outlet and aiding in the drying of the toothbrush to be conditioned.

19. A toothbrush conditioning device as in claim 17, wherein:

(a) said positioning means includes an apertured surface and a portion of said lamp means extends downwardly beyond said surface;

(b) said surface has a plurality of apertures and one of said apertures is in communication with said berth; and (c) said portion extends through said communicating aperture.

20. A toothbrush conditioning device as in claim 19, wherein:

(a) said positioning means includes dividers disposed transversely from said surface; and (b) each of said dividers is disposed between adjacent pairs of said other apertures.

* * * * *